United States Patent
Lu et al.

(10) Patent No.: US 12,089,988 B2
(45) Date of Patent: Sep. 17, 2024

(54) SYSTEMS AND METHODS FOR AUTOMATED PHYSIOLOGICAL PARAMETER ESTIMATION FROM ULTRASOUND IMAGE SEQUENCES

(71) Applicant: EchoNous, Inc., Redmond, WA (US)

(72) Inventors: Allen Lu, Seattle, WA (US); Babajide Ayinde, Redmond, WA (US)

(73) Assignee: EchoNous, Inc., Redmond, WA (US)

(*) Notice: Subject to any disclaimer, the term of this patent is extended or adjusted under 35 U.S.C. 154(b) by 240 days.

(21) Appl. No.: 17/242,064

(22) Filed: Apr. 27, 2021

(65) Prior Publication Data
US 2021/0330285 A1 Oct. 28, 2021

Related U.S. Application Data

(60) Provisional application No. 63/016,933, filed on Apr. 28, 2020.

(51) Int. Cl.
 *A61B 8/08* (2006.01)
 *G06T 7/00* (2017.01)

(52) U.S. Cl.
 CPC .......... *A61B 8/0883* (2013.01); *G06T 7/0016* (2013.01); *G06T 2207/10132* (2013.01);
 (Continued)

(58) Field of Classification Search
 CPC ....... G06T 7/0012; G06T 7/0016; A61B 8/06; A61B 8/065; A61B 8/0883; A61B 8/0833; A61B 8/52; A61B 8/5207; A61B 8/5215
 See application file for complete search history.

(56) References Cited

U.S. PATENT DOCUMENTS

2012/0078097 A1 3/2012 Wang et al.
2013/0190600 A1* 7/2013 Gupta ................. A61B 8/0866
 600/407

(Continued)

FOREIGN PATENT DOCUMENTS

KR 10-2019-0021344 A 3/2019
KR 10-2019-0105220 A 9/2019

(Continued)

OTHER PUBLICATIONS

Extended European Search Report for European Application No. 21796600.1 dated Apr. 24, 2024, 8 pages.

(Continued)

*Primary Examiner* — Carolyn A Pehlke
(74) *Attorney, Agent, or Firm* — Seed IP Law Group LLP

(57) ABSTRACT

Systems and methods for automated physiological parameter estimation from ultrasound image sequences are provided. An ultrasound system includes an ultrasound imaging device configured to acquire a sequence of ultrasound images of a patient. An anatomical structure recognition module includes processing circuitry configured to receive the acquired sequence of ultrasound images from the ultrasound imaging device, and automatically recognize an anatomical structure in the received sequence of ultrasound images. A physiological parameters estimation module includes processing circuitry configured to automatically estimate one or more physiological parameters associated with the recognized anatomical structure.

16 Claims, 3 Drawing Sheets

(52) U.S. Cl.
CPC ............... *G06T 2207/20081* (2013.01); *G06T 2207/30048* (2013.01)

(56) References Cited

U.S. PATENT DOCUMENTS

| | | | |
|---|---|---|---|
| 2018/0218502 A1* | 8/2018 | Golden | G06T 7/11 |
| 2019/0125295 A1 | 5/2019 | Tek et al. | |
| 2019/0130554 A1* | 5/2019 | Rothberg | G06T 7/0002 |
| 2020/0380675 A1* | 12/2020 | Golden | G06T 7/143 |

FOREIGN PATENT DOCUMENTS

| | | |
|---|---|---|
| KR | 10-2019-0119592 A | 10/2019 |
| WO | 2017/193251 A1 | 11/2017 |
| WO | 2017/205836 A1 | 11/2017 |
| WO | 2017/206023 A1 | 12/2017 |
| WO | 2019/178404 A1 | 9/2019 |

OTHER PUBLICATIONS

Chen, C. et al., "Deep learning for cardiac image segmentation: A review", arxiv.org, Cornell University Library, Nov. 9, 2019, 8 pages.

* cited by examiner

SYSTEMS AND METHODS FOR AUTOMATED PHYSIOLOGICAL PARAMETER ESTIMATION FROM ULTRASOUND IMAGE SEQUENCES

BACKGROUND

Technical Field

This disclosure generally relates to ultrasound imaging systems and methods and, more particularly, to artificial intelligence based networks for ultrasound imaging and evaluation of ultrasound images.

Description of the Related Art

Ultrasound is a useful medical imaging modality for assessing the health of the entire human (or animal) body. It can be used by the ultrasound user to extract useful information (e.g., ejection fraction from cardiac images) from multiple organs, including the heart, lungs, abdomen, bladder, muscles, etc. In standard clinical practice, ultrasound users would manually analyze the ultrasound data, which is subjective and can be time consuming.

BRIEF SUMMARY

With the advent of machine learning (ML), ultrasound acquisition processes may be augmented with ML-based workflow, which can both improve objectivity in analysis of ultrasound images and can improve efficiency. ML-based workflows are different from strictly machine learning models in that ML-based workflows may contain non-ML components, such as traditional image processing techniques.

A unique aspect of ultrasound data is that it typically includes of a sequence of ultrasound images of high temporal resolution obtained over a period of time. Both ML and ultrasound users typically rely on first selecting key image frames in the ultrasound image sequence that are relevant to the desired measurement, and then only those selected key images are analyzed. However, ultrasound image sequences typically contain temporal information that is relevant to the desired measurement that is not utilized by ML algorithms or ultrasound users.

The present disclosure provides systems and methods that provide significant advantages over conventional methodologies, such as by utilizing an ultrasound image sequence in estimation of a desired output, such as a clinical measurement. Feeding an ultrasound image sequence into the machine learning circuitry or ML-based workflows allows for incorporating prior information, such as periodicity for cardiac ultrasound data, which facilitates significant improvements in the performance of machine learning-based workflows.

In at least one embodiment, an ultrasound system is provided that includes an ultrasound imaging device, an anatomical structure recognition module, and a physiological parameters estimation module. The anatomical structure recognition module includes processing circuitry configured to receive an acquired sequence of ultrasound images from the ultrasound imaging device, and automatically recognize an anatomical structure in the received sequence of ultrasound images. The physiological parameters estimation module includes processing circuitry configured to automatically estimate one or more physiological parameters associated with the recognized anatomical structure.

In at least one embodiment, a system is provided that includes a machine learning model including machine learning circuitry. The machine learning circuitry is configured to: receive a sequence of ultrasound images of a patient; receive prior knowledge associated with an anatomical structure; and automatically estimate one or more physiological parameters associated with a structure observed in the sequence of the ultrasound images of a patient based at least in part on the prior knowledge.

In at least one embodiment, a method is provided that includes acquiring a sequence of ultrasound images of a patient; automatically recognizing, by anatomical structure recognition circuitry, an anatomical structure in the received sequence of ultrasound images; and automatically estimating, by physiological parameters estimation circuitry, one or more physiological parameters associated with the recognized anatomical structure.

DETAILED DESCRIPTION

The present disclosure provides several embodiments of systems and methods for automatic estimation of clinical or physiological parameters based on sequences of ultrasound images. In some embodiments, a machine learning model or workflow is provided with or otherwise accesses prior knowledge which facilitates learning by the machine learning model with less training data and results in better performance. The prior knowledge may be any knowledge relevant to the clinical or physiological parameters that are estimated by the systems and methods provided herein. In some embodiments, the prior knowledge is knowledge associated with the clinical or physiological parameters, biomechanical knowledge, ultrasound-specific knowledge (e.g., knowledge particularly associated with ultrasound imaging parameters), or the like.

In some embodiments, systems and methods are provided which automatically estimate measurements or values, which may include both clinical measurements and non-clinical quantifications of value based on a sequence of ultrasound images. Moreover, in various embodiments, a quality of images within a sequence of ultrasound images is determined, and the determined quality is utilized to select one or more images of the sequence of ultrasound images from which to estimate clinical or physiological parameters, such as ejection fraction of the heart.

Utilizing artificial intelligence approaches, the systems and methods provided herein are capable of automatically recognizing anatomical structures within acquired ultrasound images (or in a sequence of acquired ultrasound images). The recognized anatomical structures may be analyzed to estimate clinical or physiological parameters, such as ejection fraction, while an examination of a patient is being performed, and in some embodiments, the clinical or physiological parameters are automatically estimated in real-time. Artificial intelligence approaches are also utilized in the systems and methods provided herein to automatically determine an image quality grade for acquired ultrasound images, and in some embodiments, the determined image quality grade may be utilized to guide the user toward acquisition of a particular ultrasound image, such as a particular clinically desirable or standard view.

Figure 1:
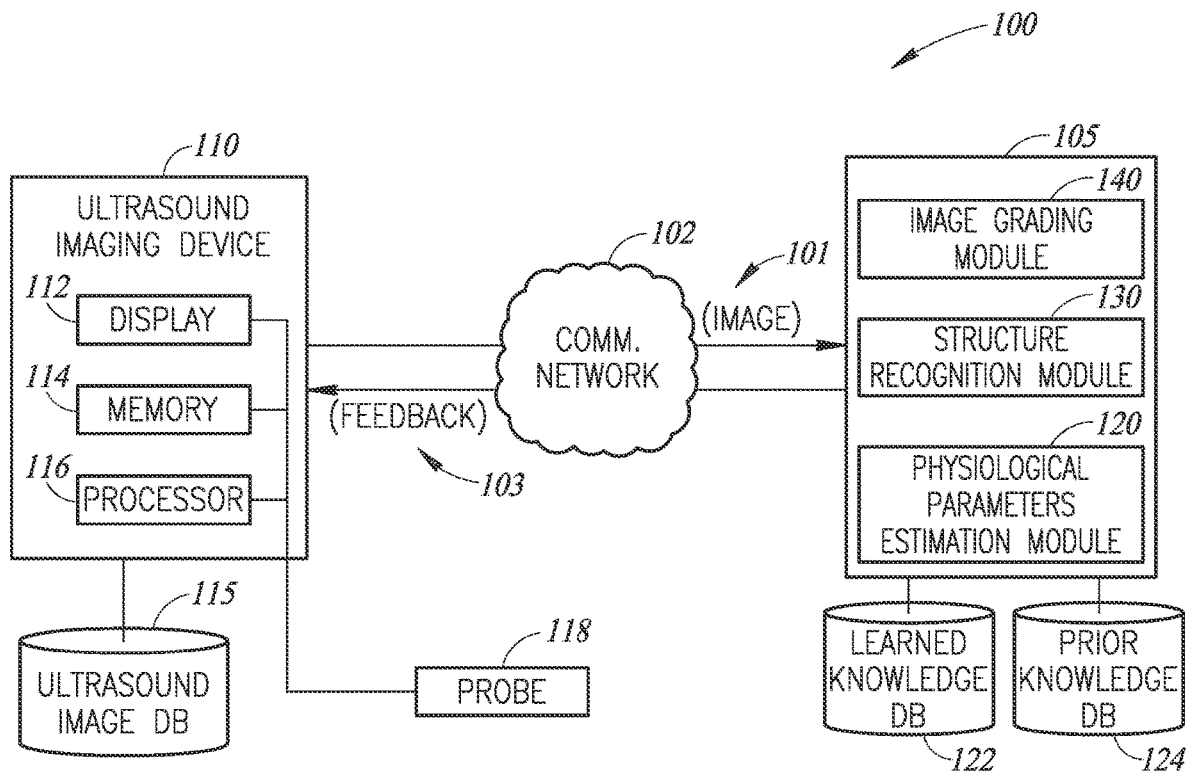
FIG. 1 is a block diagram illustrating an automated clinical or physiological parameter estimation system, in accordance with one or more embodiments of the disclosure.

FIG. 1 illustrates a block diagram of an automated clinical or physiological parameter estimation system 100 (which may be referred to herein as system 100), in accordance with embodiments of the present disclosure.

As shown in FIG. 1, the system 100 includes an ultrasound imaging device 110, a communications network 102, machine learning circuitry 105, a learned knowledge database 122 and a prior knowledge database 124. Each of these may be incorporated into a single ultrasound device, such as a hand-held or portable device, or may constitute multiple devices operatively linked or linkable to one another. As will be described in further detail herein, the machine learning circuitry 105 may include a physiological parameters estimation module 120, an anatomical structure recognition module 130, and an ultrasound image grading module 140, each of which may include programmed and/or hardwired processing circuitry configured to perform the functions or actions of the respective modules as described herein.

The ultrasound imaging device 110 is any ultrasound device operable to acquire ultrasound images of a patient, and may be, in at least some embodiments for example, a handheld ultrasound imaging device. The ultrasound imaging device 110 may include a display 112, memory 114, and one or more processors 116. The ultrasound imaging device 110 is operatively coupled to an ultrasound probe 118.

The memory 114 may be or include any computer-readable storage medium, including, for example, read-only memory (ROM), random access memory (RAM), flash memory, hard disk drive, optical storage device, magnetic storage device, electrically erasable programmable read-only memory (EEPROM), organic storage media, or the like.

The processor 116 may be any computer processor operable to execute instructions (e.g., stored in memory 114) to perform the functions of the ultrasound imaging device 110 as described herein.

The ultrasound probe 118 is driven by the ultrasound imaging device 110 to transmit ultrasound signals toward a target region in a patient, and to receive echo signals returning from the target region in response to the transmitted signals. In operation, a user of the ultrasound device 110 may hold the probe 118 against a patient's body at a position and angle to acquire a desired ultrasound image. The signals received by the probe (i.e., the echo signals) are communicated to the ultrasound imaging device 110 and may form, or be processed to form, an ultrasound image of the target region of the patient. Further, the ultrasound images may be provided to the display 112, which may display the ultrasound images and/or any other relevant information to the user.

The ultrasound images thus acquired by the ultrasound imaging device 110 may be provided to the machine learning circuitry 105 via a communications network 102. Ultrasound images from the ultrasound imaging device 110 are provided to the machine learning circuitry 105, as shown by reference numeral 101. Communications network 102 may utilize one or more protocols to communicate via one or more physical networks, including local area networks, wireless networks, dedicated lines, intranets, the Internet, and the like.

In one or more embodiments, the machine learning circuitry 105 (including, for example, the physiological parameters estimation module 120, the anatomical structure recognition module 130, and the ultrasound image grading module 140) may be provided within the ultrasound imaging device 110. In some embodiments, a local copy of the machine learning circuitry 105, knowledge stored in the learned knowledge database 122 or knowledge stored in the prior knowledge database 124 may be contained within the ultrasound imaging device 110, with the ultrasound imaging device 110 having access to a remotely located (e.g., stored on one or more server computers, or in the "cloud") machine learning circuitry 105.

The machine learning circuitry 105 may be or include any electrical circuitry configured to perform the clinical or physiological parameters estimation techniques described herein. In some embodiments, the machine learning circuitry 105 may include or be executed by a computer processor, a microprocessor, a microcontroller, or the like, configured to perform the various functions and operations described herein with respect to the machine learning circuitry 105. For example, the machine learning circuitry 105 may be executed by a computer processor selectively activated or reconfigured by a stored computer program, or may be a specially constructed computing platform for carrying out the features and operations described herein. In some embodiments, the machine learning circuitry 105 may be configured to execute software instructions stored in any computer-readable storage medium, including, for example, read-only memory (ROM), random access memory (RAM), flash memory, hard disk drive, optical storage device, magnetic storage device, electrically erasable programmable read-only memory (EEPROM), organic storage media, or the like.

The machine learning circuitry 105 receives the ultrasound images acquired by the ultrasound imaging device 110, and automatically estimates one or more clinical or physiological parameters based on the received ultrasound images. More particularly, in some embodiments, the machine learning circuitry 105 receives a sequence of ultrasound images (e.g., a video clip) acquired by the ultrasound imaging device 110, and automatically estimates one or more clinical or physiological parameters based on the received sequence of ultrasound images.

For example, in some embodiments, the anatomical structure recognition module 130 (which may be included as part of the machine learning circuitry 105) conducts an analysis of the image data in the sequence of ultrasound images and automatically recognizes anatomical structures in the sequence of ultrasound images which may be associated with one or more physiological parameters to be estimated or determined. The anatomical structure recognition module 130 may utilize any suitable technique to automatically recognize anatomical structures in the sequence of ultrasound images. For example, U.S. patent application Ser. No. 15/454,678, filed Mar. 9, 2017 and assigned to the assignee of the present disclosure and incorporated by reference herein, describes various embodiments of ultrasound image recognition systems and methods which may be included as part of the anatomical structure recognition module 130.

The recognized anatomical structures may be any anatomical structures from which one or more physiological parameters are estimated, and in some embodiments, the recognized anatomical structures may be cardiac-related structures, such as a left ventricle. However, it will be readily appreciated that any anatomical structure may be recognized by the anatomical structure recognition module 130. The recognized anatomical structures may be utilized, for example, by the physiological parameters estimation module 120 to automatically estimate one or more physiological parameters associated with, or based on an analysis of, the recognized anatomical structures. For example, in some embodiments, the anatomical structure recognition module 130 is configured to recognize the left ventricle of a heart, and the physiological parameters estimation module 120 is configured to estimate an ejection fraction based on the received sequence of ultrasound images in which the left ventricle has been recognized.

In some embodiments, the ultrasound image grading module 140 (which may be included as part of the machine learning circuitry 105) automatically determines an image quality for some or all of the received ultrasound images of the sequence of ultrasound images.

Each of the physiological parameters estimation module 120, the anatomical structure recognition module 130, and the ultrasound image grading module 140 may be implemented by a computationally intelligent system that employs artificial intelligence, drawing from the learned knowledge database 122 and the prior knowledge database 124, to perform the functions of these modules as described herein (e.g., estimating physiological parameters, recognizing anatomical structures in a sequence of ultrasound images, and determining an image quality of the ultrasound images). Some or all of the functions of the physiological parameters estimation module 120, the anatomical structure recognition module 130, and the ultrasound image grading module 140 described herein may be performed automatically by the physiological parameters estimation module 120, the anatomical structure recognition module 130, and the ultrasound image grading module 140, for example, in response to receiving the acquired sequence of ultrasound images.

"Artificial intelligence" is used herein to broadly describe any computationally intelligent systems and methods that can learn knowledge (e.g., based on training data), and automatically use such learned knowledge to adapt its approaches for solving one or more problems. Artificially intelligent machines may employ, for example, neural network, deep learning, convolutional neural network, and Bayesian program learning techniques to solve problems such as physiological parameters estimation, anatomical structure recognition, and image quality grading. Further, artificial intelligence may include any one or combination of the following computational techniques: constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing one or more computationally intelligent techniques, the machine learning circuitry 105 (e.g., including the physiological parameters estimation module 120, the anatomical structure recognition module 130, and the ultrasound image grading module 140) may learn to adapt to an unknown and/or changing environment for better performance.

The learned knowledge database 122 may include a variety of information facilitating estimation of physiological parameters, recognition of anatomical structures, and image quality determination or grading, with respect to received sequences of ultrasound images, by the physiological parameters estimation module 120, the anatomical structure recognition module 130, and the ultrasound image grading module 140. The learned knowledge stored in the learned knowledge database 122 may be learned through training of the machine learning circuitry 105, for example, as will be described in further detail later herein with respect to FIG. 2.

In some embodiments, the learned knowledge database 122 may contain information relating to various image views of various organs. For example, the learned knowledge database 122 may include information associated with clinically standard or desirable views of a heart. The clinically standard views of a heart may include, for example, suprasternal, subcostal, short- and long-axis parasternal, 2-chamber apical, 3-chamber apical, 4-chamber apical and 5-chamber apical views. Additionally, the information associated with clinically standard views may be information associated with a three-dimensional view, a two-dimensional cross section view and/or a set of two-dimensional cross section views. The information relating to various image views of a structure, such as a heart, may be utilized, for example, by the anatomical structure recognition module 130 to recognize a particular structure (e.g., left ventricle) or view of the heart within a sequence of received ultrasound images.

The learned knowledge database 122 and the prior knowledge database 124 may be stored in any computer-readable storage medium accessible by the machine learning circuitry 105, including, for example, any of the physiological parameters estimation module 120, the anatomical structure recognition module 130, and the ultrasound image grading module 140.

The prior knowledge database 124 may contain any knowledge relating to known clinical or physiological characteristics, biomechanical characteristics, ultrasound-specific characteristics or parameters (e.g., knowledge particularly associated with ultrasound imaging parameters), or the like. In some embodiments, the prior knowledge database 124 stores temporal prior knowledge which may be, for example, any known relation between temporal information observed or otherwise acquired from ultrasound images (or sequence of images). As an example, the prior knowledge database 124 may store temporal prior knowledge that indicates that a beating heart is temporally periodic, and thus a sequence of ultrasound images of a beating heart is temporally periodic. In some embodiments, the prior knowledge database 124 stores temporal prior knowledge in the form of phase information. Periodic functions, such as a cardiac cycle, have an associated phase, and the phase of such physiological functions may be stored as prior knowledge in the prior knowledge database.

In some embodiments, the prior knowledge database 124 stores spatial prior knowledge, which may be any prior knowledge associated with spatial characteristics. As an example, in some embodiments, the prior knowledge database 124 stores spatial information in the form of ultrasound image view information. The ultrasound image view information may indicate a particular view of a structure or organ, such as a particular view of a heart.

In some embodiments, the prior knowledge database 124 stores both temporal and spatial prior knowledge, collectively referred to herein as spatiotemporal prior knowledge.

Figure 2:
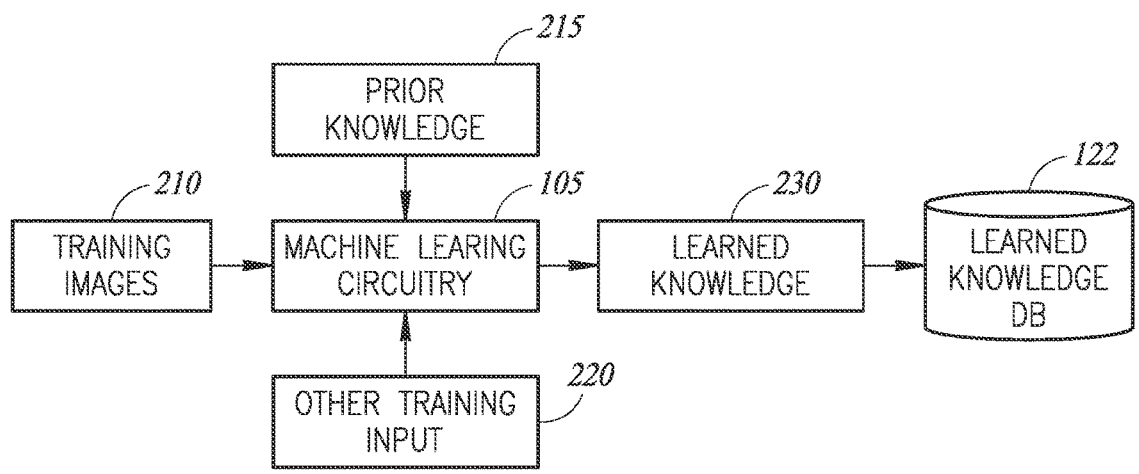
FIG. 2 is a block diagram illustrating training of the machine learning circuitry of the system shown in FIG. 1, in accordance with one or more embodiments of the disclosure.

FIG. 2 is a block diagram illustrating training of the machine learning circuitry 105, in accordance with one or more embodiments. Training of the machine learning circuitry 105 may include, in various embodiments, separate or concurrent training of each of the physiological parameters estimation module 120, the anatomical structure recognition module 130, and the ultrasound image grading module 140. Moreover, in some embodiments, each of the physiological parameters estimation module 120, the anatomical structure recognition module 130, and the ultrasound image grading module 140 may be implemented as separate machine learning models, and in other embodiments, some or all of the physiological parameters estimation module 120, the anatomical structure recognition module 130, and the ultrasound image grading module 140 may be implemented in a same machine learning model.

The machine learning circuitry 105 may be trained based on training images 210. In some embodiments, the training images 210 include videos or clips of sequential ultrasound images. The training images 210 may include any ultrasound image information. For example, the training images 210 may include image information used to train the anatomical structure recognition module 130, such as a variety of ultrasound image information associated with known views of an organ, such as the heart. As a further example, the training images 210 may be clinically desirable images of, e.g., apical 4-chamber (A4C) views of a heart. In such a case, the training images 210 may be ultrasound images which have been pre-determined (e.g., by a physician) as adequately showing a clinically desirable A4C view of a heart. Each such training image or sequence of training images 210 may have slightly different characteristics (e.g., higher quality images, lower quality images, blurry images, images taken at slightly different angles, and so on), yet each such training image 210 may nonetheless be pre-determined as adequately representing a clinically desirable view of a heart or other anatomical structure. The training images 210 may also have quality scores associated therewith indicating a relative level of quality in terms of representing clinically standard or desirable views.

Moreover, the training images 210 may include not only image information associated with clinically standard or desirable views, but may further include image information associated with non-clinically desirable views. Accordingly, the anatomical structure recognition module 130 may receive, for example, a view of a heart which is not representative of any particular clinically desirable view (e.g., suprasternal, subcostal, short- and long-axis parasternal, 2-chamber apical, 3-chamber apical, 4-chamber apical and 5-chamber apical views) and thus be trained to recognize views that are not clinically desirable. In such a case, the anatomical structure recognition module 130 may nonetheless be trained to recognize the image or sequence of images as representative of a view of a heart, and may further recognize the image or sequence of images as being somewhere between, for example, a 2-chamber apical view and a 3-chamber apical view. A clinically standard 3-chamber apical view is generally obtainable, for example, by rotating an ultrasound imaging probe about 60° counterclockwise with respect to the 2-chamber apical view. Ultrasound images obtained with the probe at an angle of rotation somewhere between, for example, 5° and 55° counterclockwise with respect to the 2-chamber apical view may be determined as not representing a clinically desirable view of the heart. The anatomical structure recognition module 130 may be trained with training images 210 showing a variety of known, but non-clinically desirable, views of a heart (such as views somewhere between the 2-chamber apical and the 3-chamber apical views), and thus may recognize such views (e.g., the ultrasound image recognition module 120 may recognize a view as representing a 35° counterclockwise rotation of the probe 118 with respect to the 2-chamber apical view).

In some embodiments, the training images 210 may include a variety of ultrasound image information associated with known anatomical structures, such as particular organs (e.g., the heart) or particular features of organs (e.g., left ventricle, right ventricle, left atrium, right atrium, mitral valve, tricuspid valve, aortic valve, etc.), and such ultrasound image information may be used to train the anatomical structure recognition module 130. Further, the training images 210 may include image information associated with such known anatomical structures from a variety of different views. Anatomic structures may appear very different across different views, e.g., the left ventricle may appear different in ultrasound images acquired at various different views (e.g., apical-LV, parasternal long-LV, parasternal long-LV). Therefore, ultrasound images representing known anatomic structures (e.g., the left ventricle) in a variety of different views may be provided as training images 210, which may be utilized to train the anatomical structure recognition module 130 to recognize not only the anatomical structure but also the particular view provided by the ultrasound image.

In some embodiments, the training images 210 may include image information used to train the ultrasound image grading module 140. For example, the training images 210 may include a variety of ultrasound images of different image qualities (e.g., higher quality images, lower quality images, blurry images, and so on). The qualities of the training images 210 used to train the ultrasound image grading module 140 may be graded, for example, by an expert such as a physician or other clinician. The qualities of the training images 210 may be graded based on any grading system. In some embodiments, the qualities of the training images 210 may be graded based on a standard grading system, such as the American College of Emergency Physicians (ACEP) grading rubric.

Other training input 220 may further be provided to the ultrasound image recognition module 120 for training. The other training input 220 may include, for example, manually-entered input to adjust or otherwise manage the machine learning model, or parameters thereof, developed through the training process.

Prior knowledge 215 may further be utilized as input to train the machine learning circuitry 105. The prior knowledge 215 may include any knowledge relating to known clinical or physiological characteristics, biomechanical characteristics, ultrasound-specific characteristics or parameters (e.g., knowledge particularly associated with ultrasound imaging parameters), or the like. In some embodiments, the prior knowledge 215 includes spatiotemporal prior knowledge which may include phase information or knowledge, ultrasound image view information or knowledge, or any other temporal or spatial prior knowledge. The prior knowledge 215 may be or include any prior knowledge associated with any rules or constraints, which may be explicitly or implicitly defined. The prior knowledge 215 may be incorporated in the training of the machine learning circuitry 105 (e.g., as shown in FIG. 2), and further may be utilized by the machine learning circuitry 105 for inference (e.g., for estimating physiological parameters, recognizing anatomical structures in a sequence of ultrasound images, and determining an image quality of the ultrasound images).

Using training images 210, the machine learning circuitry 105 (including the physiological parameters estimation module 120, the anatomical structure recognition module 130, and the ultrasound image grading module 140) may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

Figure 3:
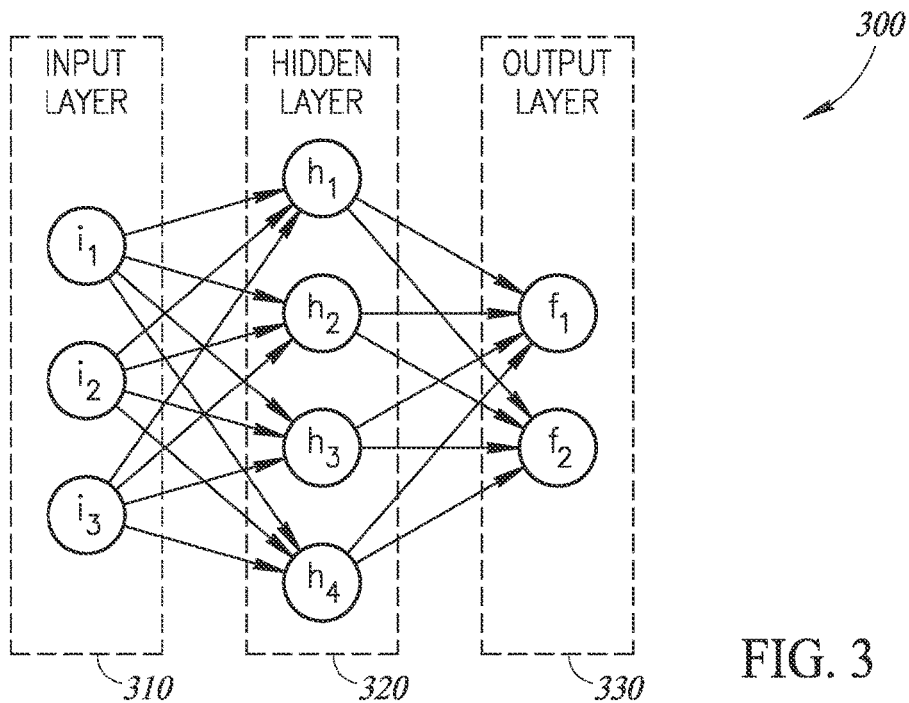
FIG. 3 is a block diagram illustrating a neural network, which may be implemented by the machine learning circuitry, in accordance with one or more embodiments of the disclosure.

The back-propagation learning algorithm is a common method of training artificial neural networks (and may be employed, for example, with the artificial neural network 300 shown in FIG. 3). Back-propagation generally includes two phases: propagation and weight update. In the propagation phase, a training pattern's input is forward propagated through the neural network in order to generate the propagation's output activations. Then, the propagation's output activations are backward propagated through the neural network using the training pattern target in order to generate deltas (i.e., the difference between the input and output values) of all output and hidden neurons. In the weight update phase, for each weight-synapse the following steps are generally performed: 1. Multiply its output delta and input activation to get the gradient of the weight; 2. Subtract a ratio (percentage) of the gradient from the weight. The propagation and weight update phases are repeated as desired until performance of the network is satisfactory.

As a result of the training, the physiological parameters estimation module 120, the anatomical structure recognition module 130, and the ultrasound image grading module 140 may learn to modify their behavior in response to the training images 210 and the prior knowledge 215, and obtain or generate learned knowledge 230. The learned knowledge 230 may represent any information upon which the physiological parameters estimation module 120, the anatomical structure recognition module 130, and the ultrasound image grading module 140 may utilize to determine an appropriate response to new data or situations. For example, the learned knowledge 230 may represent relationships between sequences of ultrasound images and anatomical structures, views of anatomical structures, image quality of the sequences of ultrasound images or the like (e.g., one or more functions that describe or predict the presence of anatomical structures in the received ultrasound images, views of anatomical structures, or image quality based on ultrasound image parameters, coefficients, weighting information, parameters associated with the example neural network shown in FIG. 3 or any such variable). The learned knowledge 230 may be stored in the learned knowledge database 122.

Based on the training images 210 and the prior knowledge 215, the physiological parameters estimation module 120, the anatomical structure recognition module 130, and the ultrasound image grading module 140 may learn to modify their behavior, and may apply knowledge contained in the learned knowledge database 122 to alter the manner in which these modules make determinations with respect to new input, such as, for example, ultrasound image information (e.g., a sequence of ultrasound images) received from the ultrasound imaging device 110.

FIG. 3 is a block diagram illustrating one example of an artificial neural network 300, which may be implemented by the machine learning circuitry 105, in accordance with one or more embodiments. In some embodiments, each of the physiological parameters estimation module 120, the anatomical structure recognition module 130, and the ultrasound image grading module 140 may be implemented by a neural network, such as the neural network 300 shown in FIG. 3. Artificial neural networks (ANNs) are artificial intelligence models that are used to estimate or approximate functions that can depend on a large number of inputs, and which are generally unknown. Such neural networks generally include a system of interconnected "neurons" which exchange information between each other. The connections have numeric weights that can be tuned based on experience, and thus neural networks are adaptive to inputs and are capable of learning.

The artificial neural network 300 shown in FIG. 3 includes three layers: an input layer 310 including input neurons $i_1$ through $i_3$, a hidden layer 320 including hidden layer neurons $h_1$ through $h_4$, and an output layer 330 including output neurons $f_1$ and $f_2$. While the neural network 300 of FIG. 3 is shown having three layers, it should be readily appreciated that additional layers may be included in the neural network 300 as desired to achieve optimal training and performance of the machine learning circuitry 105. Similarly, the neurons in each layer are shown for exemplary purposes, and it should be readily understood that each layer may include more, even significantly more, neurons than shown in FIG. 3.

The neural network 300 may be trained by providing training images 210 to the input layer 310. As described with respect to FIG. 2, the training images may include ultrasound image information having a wide variety of known characteristics, including, for example, various organ views, various known anatomical structures at various different imaging views, various image qualities or grades, and so on. Through training, the neural network 300 may generate and/or modify the hidden layer 320, which represents weighted connections mapping the training images 210 provided at the input layer 310 to known output information at the output layer 330 (e.g., classification of an image as a particular imaging view of a heart, recognition of a particular anatomical structure in an image, classification of an image as having a particular image quality, recognition of temporal or spatial relationships among ultrasound images of a sequence of ultrasound images, and the like). Relationships between neurons of the input layer 310, hidden layer 320 and output layer 330, formed through the training process and which may include weight connection relationships, are generally referred to herein as learned knowledge, and may be stored, for example, in the learned knowledge database 122.

Once the neural network 300 has been sufficiently trained, the neural network 300 may be provided with new (non-training) ultrasound images at the input layer 310 (i.e., a sequence of ultrasound images taken of a patient utilizing the ultrasound imaging device 110). Utilizing ultrasound image knowledge stored in the learned knowledge database 122 (which may include, for example, weighted connection information between neurons of the neural network 300), the neural network 300 may make determinations about the received ultrasound image information at the output layer 330. For example, the neural network 300 may recognize one or more anatomical structures in the received ultrasound images, may automatically determine an image quality or image quality grade of the received ultrasound images, and may automatically estimate one or more physiological parameters based on the received ultrasound images.

The neural network 300 of FIG. 3 is provided as just one example, among various possible implementations of the machine learning circuitry 105 which employs artificial intelligence to make determinations with respect to received ultrasound image information. For example, the machine learning circuitry 105 (including one or more of the physiological parameters estimation module 120, the anatomical structure recognition module 130, and the ultrasound image grading module 140) may implement any of neural network, deep learning, convolutional neural network, and Bayesian program learning techniques to make determinations with respect to received ultrasound images of a patient.

Figure 4:
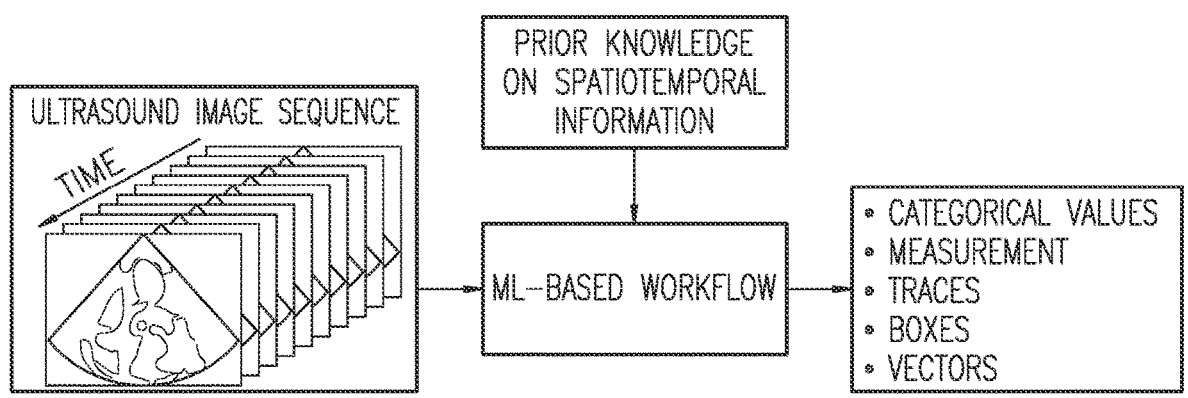
FIG. 4 is a block diagram illustrating training of the machine learning circuitry, in accordance with one or more embodiments of the disclosure.

FIG. 4 is a block diagram illustrating training of the machine learning circuitry 105 ("ML-based Workflow"), in accordance with one or more embodiments of the present disclosure. FIG. 4 is similar to the block diagram shown in FIG. 2. As shown in FIG. 4, an ultrasound image sequence is provided as training input to the ML-based workflow. Additionally, prior knowledge is provided as training input to the ML-based workflow. A difference between the block diagrams shown in FIG. 4 and FIG. 2 is that the output of the ML-based workflow of FIG. 4 is not learned knowledge, but instead is an output of the machine learning circuitry 105 once it has been trained. For example, the output of the machine learning circuitry 105 (ML-based workflow) may be any categorical values, measurements such as physiological measurements or estimates (e.g., ejection fraction, collapsibility index of the Inferior Vena Cava (IVC), estimating cardiac chamber dimensions, inference on lung ultrasound data, etc.), contours (e.g., of anatomical structures within the received ultrasound image sequence), bounding boxes, vector fields, or the like.

As shown in FIG. 4, an ultrasound image sequence is fed into the machine learning-based workflow. This allows the ML-based workflow to incorporate spatiotemporal prior information into the machine learning prediction from the ultrasound image sequence.

For example, by feeding an entire ultrasound image sequence into the ML-based workflow, temporal knowledge about the problem (e.g. temporal constraints) may be incorporated into the machine learning-based workflow. Incorporating temporal knowledge allows the ML model to learn with less training data and better performance.

In general, the objective of training the ML model incorporating spatiotemporal information can be formulated as follows:

$$\mathrm{argmax}_\theta \mathcal{L}(\theta|X,Y)+P(\theta,X,Y),$$

where $\mathcal{L}$ represents a likelihood function, $\theta$ represents the parameters of the machine learning model in the workflow, X represents the input image sequence with M image frames: $X=\{x_t, t=1: M\}$, and $Y=\{y_t, t=1: N\}$ represents the sequence of desired outputs. In other words, X and Y represent the data for machine learning model training. N may be equal to M, which means the machine learning model would predict at least one output per image frame. On the other extreme, N may be equal to 1, which means the machine learning model would predict one value for the entire image sequence. $P(\theta, X, Y)$ represents the prior function, which represents the prior information or prior knowledge that is known about the distribution of machine learning model parameters ($\theta$), sequence of images (X), or sequence of desired output (Y). This function enforces certain constraints on $\theta$, X, and Y that allows the network to more easily find the optimal $\theta$ or network parameters. This function may be a direct mathematical term to be incorporated into the objective function, or it can be applied to the ML-based workflow as a pre-processing or post-processing step. After the machine learning model within the workflow is trained, for inference, an entire image sequence may be fed into the workflow for improved performance.

As an example, this approach may be applied to the task of estimating ejection fraction in accordance with some embodiments of the present disclosure. Ejection fraction is a clinical measurement for measuring the systolic function of the heart. It is estimated using two key frames: end-diastole (ED) and end-systole (ES) frames. In some embodiments of the present disclosure, prior information or prior knowledge is utilized that X is periodic for a cardiac image sequence. Therefore, $x(t)=x(t+T)$ where T is the period. Hence, $x(ED)=x(ED+T)$ for all the ED frames in the image sequence. The same applies to the ES frame as well. Thus, after feeding the entire image sequence into the ML-based workflow, the workflow estimates and segments all pairs of ED and ES frames in the image sequence for computing the final ejection fraction.

This design is highly generalizable to a number of ultrasound applications. For example, the temporal consistency prior knowledge can be represented and enforced mathematically by minimizing $\|y(t)-y(t-1)\|$ as part of the objective function for training the machine learning model in the workflow. This particular framework is applicable for all types ultrasound sequence data.

Traditional designs of ML-based workflows would first divide the ultrasound image sequence into individual frames and perform inference on the individual frames. Then, post-processing logic would be used to combine the inference results from the individual frames into a final value. In contrast, the system illustrated in FIG. 4 incorporates the entire input ultrasound image sequence and imposes prior knowledge for the temporal dimension (in mathematical or algorithmic terms) to the machine learning model (within the ML-based workflow) training process. As a result, an entire image sequence may be fed into the ML-based workflow during inference.

The temporal prior knowledge (e.g., that X is periodic for a cardiac image sequence) may be utilized by the ML-based workflow to enforce a prediction that each successive frame of the sequence of ultrasound images should be very close to one another (e.g., in similarity and image appearance). Thus, successive outputs (Y) should also be very similar to each other.

As noted previously herein, the term $P(\theta, X, Y)$ represents the prior function, which uses prior knowledge, e.g., prior knowledge of both X and Y. In the example of estimating ejection fraction, X may indicate that ejection fraction is periodic. In some embodiments, prior knowledge can also be provided with respect to network parameters ($\theta$).

In some embodiments, prior knowledge relating to phase is fed into the ML-based workflow. Phase is a function of X (which is periodic). The phase information may be utilized to determine which frames out of the received video clip or sequence of ultrasound images represent the two frames (end-diastole (ED) and end-systole (ES) frames) utilized (e.g., by the physiological parameters estimation module 120) to estimate ejection fraction.

In some embodiments, ultrasound view information may be utilized as prior knowledge that is fed into the ML-based workflow. View information may include, for example, information associated with a particular angle that the received sequence of ultrasound images represent of a structure such as the A4C view of a heart. The view information is prior knowledge that can be used to estimate physiological parameters, such as to estimate or compute ejection fraction.

In some embodiments, the image quality (e.g., as determined by the ultrasound image grading module 140) of the received ultrasound images may be utilized (e.g., by the anatomical structure recognition module 130 or the physiological parameters estimation module 120) to select one or more ultrasound images within the received sequence of ultrasound images for use in estimating the one or more physiological parameters. For example, in some embodiments, image quality is utilized to select one or more ultrasound images associated with the cardiac cycle that provides a best quality for computing ejection fraction. The selected ultrasound images may be selected based on having a quality that is above a threshold quality. For example, in some embodiments, only ultrasound images having a suitable quality (e.g., above a threshold quality level) are utilized for estimating the physiological parameters associated with the recognized structure (e.g., the ejection fraction of a heart).

In various embodiments, the determined quality may be a quality of an entire sequence or clip of ultrasound images, or a quality of specific images or frames of the sequence of ultrasound images. In some embodiments, the ultrasound image grading module 140 determines quality at the frame-level (e.g., quality is determined for each frame of a sequence of ultrasound images), then the quality at the frame-level is associated with an entire clip or sequence of ultrasound images of a heart to estimate the ejection fraction.

In some embodiments, persistence is applied to the determined quality of the ultrasound images. For example, in some embodiments, the determined image quality represents a quality of a current (e.g., most recently acquired) frame or ultrasound image, but it may be based at least in part on determined qualities of one or more prior frames or prior ultrasound images of the acquired sequence of ultrasound images. In some embodiments, the determined quality of the received ultrasound images is stored in a buffer, so the quality of a most recent or current ultrasound image may be weighted or averaged based on a selected number of prior ultrasound image qualities stored in the buffer.

In some embodiments, the determined quality is based on image clarity (e.g., image settings and brightness, ultrasound imaging parameters, etc.) and view (e.g., the geometry of the structure; does the view accurately portray the expected structures).

Figure 5:
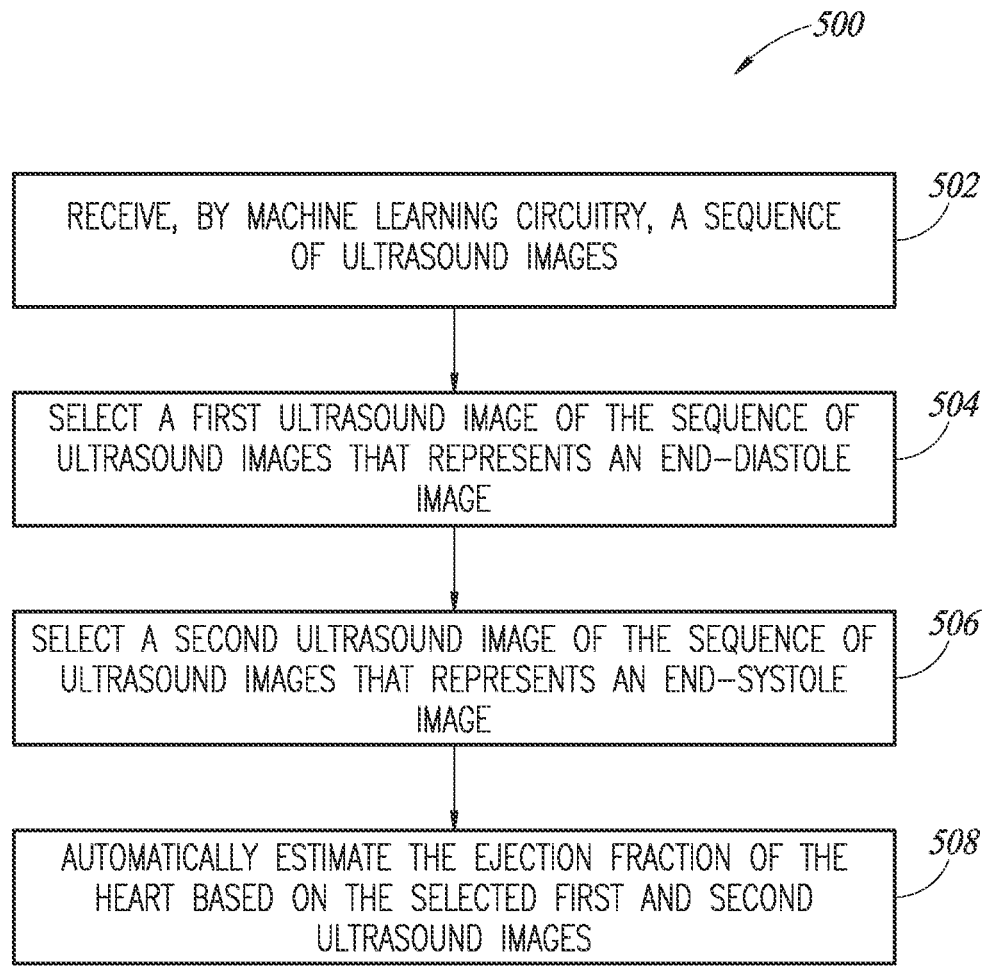
FIG. 5 is a flow chart illustrating a process for detecting end-diastole (ED) and end-systole (ES) frames from an A4C or A2C clip or sequence of ultrasound images, in accordance with one or more embodiments of the disclosure.

FIG. 5 is a flow chart 500 illustrating a process for detecting end-diastole (ED) and end-systole (ES) frames from an A4C or A2C clip or sequence of ultrasound images. ED and ES frames may be defined as the image frames in a clip for which the left ventricle (LV) area is the largest and smallest, respectively.

As shown in FIG. 5, at 502 a sequence of ultrasound images is received by the machine learning circuitry 105. In some embodiments, the received sequence of ultrasound images are representative of an A4C or A2C view of a heart.

At 504, a first ultrasound image of the sequence is selected, e.g., by the machine learning circuitry 105, that represents an end-diastole image. The machine learning circuitry 105 may select the end-diastole image based at least in part on the quality of the images, for example, as described previously herein.

At 506, a second ultrasound image of the sequence is selected, e.g., by the machine learning circuitry 105, that represents an end-systole image. The machine learning circuitry 105 may select the end-systole image based at least in part on the quality of the images, for example, as described previously herein.

At 508, the ejection fraction of the heart is automatically estimated based on the selected first and second ultrasound images. The ejection fraction may be automatically estimated, for example, by the machine learning circuitry 105 implementing any of the techniques previously described herein.

In some embodiments, the machine learning circuitry 105 is trained based on sequences of ultrasound images instead of single frames, which facilitates learning of both image appearance features and motion-based features. The learned image appearance features and motion-based features may be utilized by the machine learning circuitry at 504 and 506 for selecting the end-diastole and end-systole images.

In some embodiments, one or more anatomical structures that are adjacent to an anatomical structure of interest may be included to provide additional anatomical context to the machine learning model for detecting or recognizing the anatomical structure of interest within a sequence of ultrasound images. For example, in some embodiments, the left ventricle is the anatomical structure of interest, as the left ventricle is utilized to detect the ED and ES frames from which the ejection fraction is estimated. One or more structures adjacent to the left ventricle may be utilized to aid in recognizing or detecting the presence of the left ventricle in the received ultrasound images, as the recognized presence of the one or more adjacent structures within an ultrasound image provides additional anatomical context to the machine learning circuitry 105 for detecting the presence of the left ventricle (LV).

While the machine learning circuitry 105 (including the physiological parameters estimation module 120, the anatomical structure recognition module 130, and the ultrasound image grading module 140) has been described herein as being separate from the ultrasound imaging device 110, and accessible via the communications network 102, it should be readily appreciated that the machine learning circuitry 105 may be included within the ultrasound imaging device 110. That is, the machine learning circuitry 105 (including the physiological parameters estimation module 120, the anatomical structure recognition module 130, and the ultrasound image grading module 140) may be contained within the ultrasound imaging device 110, and may be stored, for example, in memory 114 and the features and/or functionality of the machine learning circuitry 105 may be executed or otherwise implemented by the processor 116.

In some embodiments, one or more of the physiological parameters estimation module 120, the anatomical structure recognition module 130, and the ultrasound image grading module 140 may be implemented by a single neural network that is optimized for real-time performance on a mobile device. For example, one or more of the physiological parameters estimation module 120, the anatomical structure recognition module 130, and the ultrasound image grading module 140 may be implemented by a single neural network that is executed by or stored on the ultrasound imaging device 110, and the ultrasound imaging device 110 may be a mobile device such as a laptop or tablet computer, a smart phone, or the like.

In some embodiments, the estimated physiological parameters are automatically displayed, for example on the display 112 of the ultrasound imaging device 110. For example, in some embodiments, the estimated physiological parameters includes the ejection fraction of a heart, and the ejection fraction is displayed on the display 112 of the ultrasound imaging device.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultrasound system, comprising:
an ultrasound imaging device configured to acquire a sequence of ultrasound images of a patient; and
an anatomical structure recognition module including processing circuitry configured to:
receive the sequence of ultrasound images from the ultrasound imaging device; and
automatically recognize an anatomical structure in the sequence of ultrasound images;
an ultrasound image quality module including processing circuitry configured to determine a quality of the sequence of ultrasound images; and
a physiological parameters estimation module including processing circuitry configured to automatically estimate one or more physiological parameters associated with the anatomical structure,
wherein the ultrasound system includes one or more machine learning models to implement the anatomical structure recognition module and the physiological parameters estimation module, wherein the one or more machine learning models are configured to:
receive the sequence of ultrasound images of the patient as an input ultrasound image sequence; and
during an inference process, automatically operate on the entire input ultrasound image sequence as a whole to output an inference that estimates the one or more physiological parameters associated with the anatomical structure,
wherein the inference process is based at least in part on prior knowledge that was imposed on the one or more machine learning models during training,
wherein the prior knowledge includes spatiotemporal prior knowledge that is associated with the anatomical structure and indicative of a periodic relationship between the anatomical structure and the sequence of ultrasound images, the periodic relationship being utilized to enforce a prediction that each successive frame of the sequence of ultrasound images should appear similar in image appearance,
wherein the one or more machine learning models are configured to automatically estimate the one or more physiological parameters based at least in part on the quality of the sequence of ultrasound images, and
wherein the inference process includes feeding the entire input ultrasound image sequence as a whole to the one or more machine learning models to output the inference that estimates the one or more physiological parameters.

2. The ultrasound system of claim 1, wherein the ultrasound image quality module is configured to determine a quality of ultrasound images in the sequence of ultrasound images.

3. The ultrasound system of claim 2, wherein the physiological parameters estimation module is configured to automatically estimate the one or more physiological parameters based on one or more ultrasound images of the anatomical structure having a determined quality that exceeds a threshold quality level.

4. The ultrasound system of claim 2, wherein the ultrasound image quality module is configured to determine the quality of the sequence of ultrasound images based on a clarity of the ultrasound images and a view of the ultrasound images.

5. The ultrasound system of claim 2, wherein the ultrasound image quality module is configured to determine a quality of each ultrasound image of the sequence of ultrasound images.

6. The ultrasound system of claim 5, wherein the ultrasound image quality module is configured to determine a quality of a current ultrasound image based at least partially on determined qualities of prior ultrasound images of the sequence of ultrasound images.

7. The ultrasound system of claim 2, wherein the ultrasound image quality module is configured to determine a quality of a current ultrasound image based at least in part on a determined quality of one or more prior ultrasound images.

8. The ultrasound system of claim 1, wherein the anatomical structure recognition module is configured to automatically recognize a left ventricle of a heart, and the physiological parameters estimation module is configured to automatically estimate an ejection fraction of the heart.

9. The ultrasound system of claim 1, wherein the anatomical structure is a heart having a periodic cardiac cycle, and the one or more machine learning models are configured to automatically estimate an ejection fraction of the heart.

10. The ultrasound system of claim 9, wherein the one or more machine learning models are configured to:
select a first ultrasound image of the sequence of ultrasound images that represents an end-diastole image;
select a second ultrasound image of the sequence of ultrasound images that represents an end-systole image; and
automatically estimate the ejection fraction of the heart based on the selected first and second ultrasound images.

11. The ultrasound system of claim 1, wherein the anatomical structure depicted in the sequence of ultrasound images is a left ventricle, and the one or more machine learning models are configured to automatically recognize the left ventricle based at least in part on the presence of one or more structures adjacent to the left ventricle in the sequence of ultrasound images.

12. A method, comprising:
acquiring a sequence of ultrasound images of a patient;
automatically recognizing, by anatomical structure recognition circuitry, an anatomical structure in the sequence of ultrasound images;
automatically determining, by ultrasound image quality circuitry, a quality of the sequence of ultrasound images; and
automatically estimating, by physiological parameters estimation circuitry, one or more physiological parameters associated with the anatomical structure,
wherein the anatomical structure recognition circuitry and the physiological parameters estimation circuitry utilize one or more machine learning models, the one or more machine learning models being configured to:

receive the sequence of ultrasound images of the patient as an input ultrasound image sequence; and during an inference process, automatically operate on the entire input ultrasound image sequence as a whole to output an inference that estimates the one or more physiological parameters associated with the anatomical structure, wherein the inference process is based at least in part on prior knowledge that was imposed on the one or more machine learning models during training, wherein the prior knowledge includes spatiotemporal prior knowledge associated with the anatomical structure and indicative of a periodic relationship between the anatomical structure and the sequence of ultrasound images, the periodic relationship being utilized to enforce a prediction that each successive frame of the sequence of ultrasound images should be close in image appearance, wherein the one or more machine learning models are configured to automatically estimate the one or more physiological parameters based at least in part on the quality of the sequence of ultrasound images, and wherein the inference process includes feeding the entire input ultrasound image sequence as a whole to the one or more machine learning models to output the inference that estimates the one or more physiological parameters.

13. The method of claim 12, further comprising:

determining, by the ultrasound image quality circuitry, a quality of ultrasound images in the sequence of ultrasound images; and selecting one or more ultrasound images from which to automatically estimate the one or more physiological parameters associated with the anatomical structure, wherein the one or more ultrasound images are selected based on having a quality that is above a threshold quality.

14. The method of claim 12, wherein the automatically recognizing an anatomical structure includes automatically recognizing a left ventricle of a heart, and wherein the automatically estimating one or more physiological parameters includes automatically estimating an ejection fraction of the heart.

15. The method of claim 12, wherein the automatically estimating one or more physiological parameters includes automatically estimating a collapsibility index of an Inferior Vena Cava (IVC).

16. The ultrasound system of claim 7, wherein the quality of the current ultrasound image is a weighted or averaged value based on the determined quality of a selected number of prior ultrasound images.

* * * * *